US012300380B2

(12) United States Patent
Croghan

(10) Patent No.: US 12,300,380 B2
(45) Date of Patent: May 13, 2025

(54) HEALTHCARE METHODS AND SYSTEMS WITH DRIVE THROUGH BUILDING STRUCTURE/ARCHITECTURE

(71) Applicant: John E. Croghan, Kenilworth, IL (US)

(72) Inventor: John E. Croghan, Kenilworth, IL (US)

(*) Notice: Subject to any disclaimer, the term of this patent is extended or adjusted under 35 U.S.C. 154(b) by 0 days.

(21) Appl. No.: 17/105,999

(22) Filed: Nov. 27, 2020

(65) Prior Publication Data

US 2021/0158950 A1  May 27, 2021

Related U.S. Application Data

(60) Provisional application No. 62/941,566, filed on Nov. 27, 2019.

(51) Int. Cl.
*G16H 40/20* (2018.01)
*E04H 14/00* (2006.01)
*G06Q 50/22* (2018.01)
*G16H 10/60* (2018.01)
*G16H 40/63* (2018.01)

(52) U.S. Cl.
CPC ............ *G16H 40/20* (2018.01); *E04H 14/00* (2013.01); *G06Q 50/22* (2013.01); *G16H 10/60* (2018.01); *G16H 40/63* (2018.01)

(58) Field of Classification Search
CPC ........ G16H 40/20; G16H 10/60; G16H 40/63; G06Q 50/22; E04H 3/04; E04H 6/02; E04H 3/08; E04H 14/00
See application file for complete search history.

(56) References Cited

U.S. PATENT DOCUMENTS

| | | | | |
|---|---|---|---|---|
| 4,884,662 A | * | 12/1989 | Cho | ........................... E04H 3/04 186/36 |
| 4,901,482 A | * | 2/1990 | Lockard | .................. E04H 14/00 52/33 |
| 2002/0087361 A1 | | 7/2002 | Benigno et al. | |
| 2003/0195768 A1 | | 10/2003 | Taylor | |
| 2014/0246876 A1 | | 9/2014 | Blackwell et al. | |
| 2015/0261918 A1 | * | 9/2015 | Thornbury, Jr. | ........ G16H 80/00 705/3 |
| 2016/0348387 A1 | | 12/2016 | Geiger | |
| 2017/0032092 A1 | | 2/2017 | Mink et al. | |
| 2017/0094947 A1 | * | 4/2017 | Greer | ....................... E04H 1/06 |

OTHER PUBLICATIONS

Weiss, Eric A., et al. "Drive-through medicine: a novel proposal for rapid evaluation of patients during an influenza pandemic." Annals of emergency medicine 55.3 (2010): 268-273. (Year: 2010).*

(Continued)

*Primary Examiner* — Mark Holcomb
(74) *Attorney, Agent, or Firm* — Charles T. Riggs, Jr.

(57) ABSTRACT

A method and system for drive through medicine comprises a building having a service area and one or more consult bays attached to the service area, which allow users to drive in and engage a healthcare professional and/or a technician in privacy. The user will visit or consult with a doctor or other medical professional, on site and/or remotely via telemedicine. In use, a patient checks in at a patient kiosk, the patient drives into the consult bay, the patient consults with a patient advisor, the patient pays the bill and receives treatment, and the patient drives out of consult bay.

15 Claims, 21 Drawing Sheets

(56) References Cited

OTHER PUBLICATIONS

Cameron Bruce Associates "Drive-Through Medicine", Santa Clara Valley Health & Hospital System, available at https://www.calhospitalprepare.org/sites/main/files/file-attachments/drive-throughtriage_county_template_11-23-2009.pdf (Year: 2009).*

International Search Report (2 pages) and Written Opinion of the International Searching Authority (5 pages) mailed Mar. 1, 2021 in PCT/US2020/062515 (7 total pages).

Rafal M. "First in America Drive Thru Clinic, 54 Orland Square Drive, Orland Park, IL." In: www.youtube.com Jan. 29, 2016, from https://www.youtube.com/watch?v=42m_5q5YFJ4 (screenshot attach as retrieved on Jan. 24, 2021 by ISA).

Potter et al. "Modeling workplace contact networks: The effects of organizational structure, architecture, and reporting errors on epidemic predictions." In: Network Science. Jul. 31, 2015.

* cited by examiner

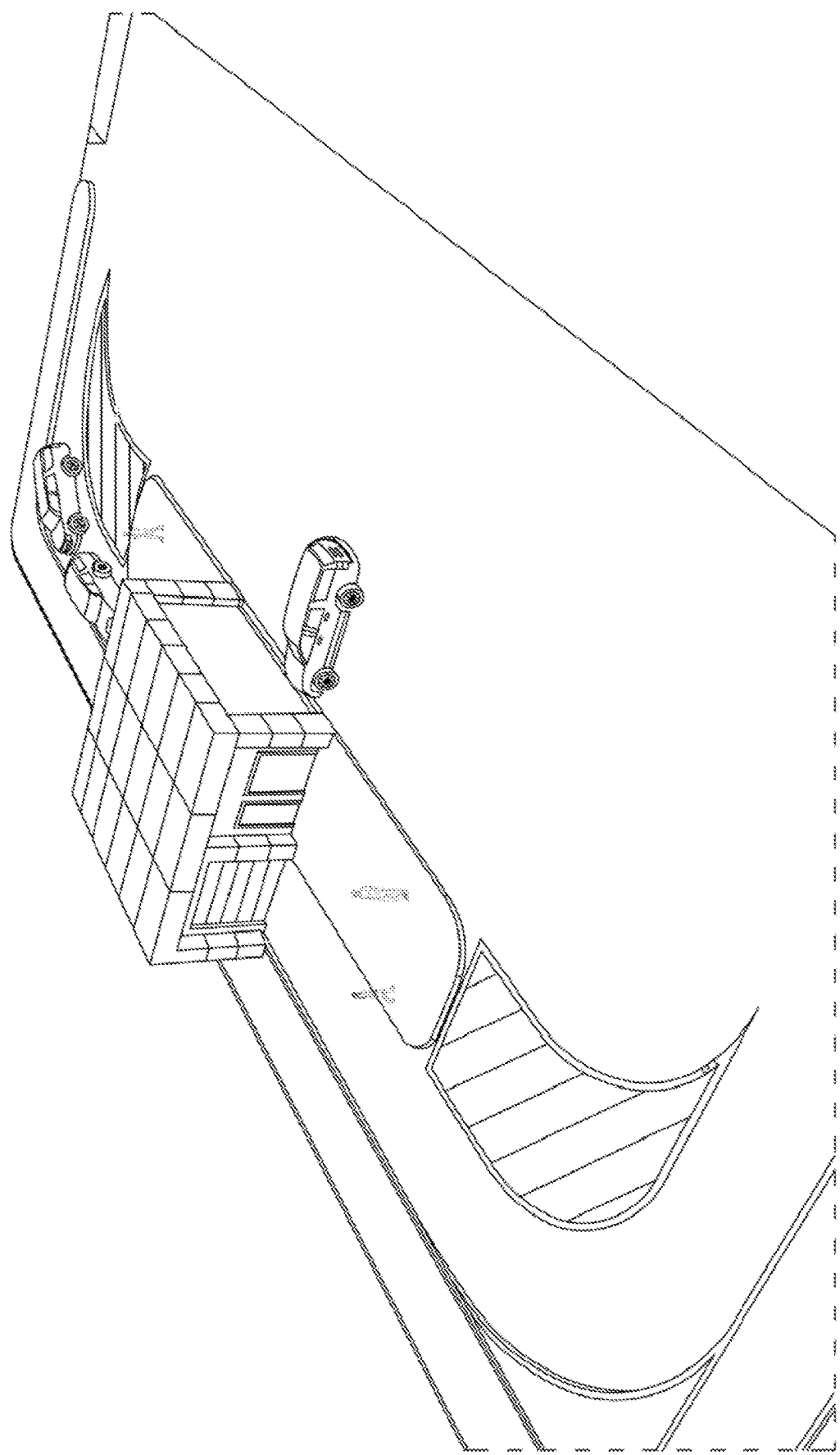

VITA

LITE

VICI

HEALTHCARE METHODS AND SYSTEMS WITH DRIVE THROUGH BUILDING STRUCTURE/ARCHITECTURE

TECHNICAL FIELD

The exemplary teachings herein pertain to methods, systems and building structures/architecture for providing healthcare and expedited medical services.

BACKGROUND

US healthcare is a broken industry. In particular, the primary care segment of the healthcare market, which typically acts as the first point of contact for patients, is plagued by ambiguous costs, inconvenience, and inconsistent access. Existing urgent care clinics are time consuming (often over an hour in wait time) and expensive (frequently copay and deductibles result in out-of-pocket cost exceeding $100).

At nearly 20% of GDP, healthcare is massive, among the largest industries in the United States. However, the healthcare business suffers from enormous inefficiency, plagued by time-consuming, over-priced connections. American consumers and employers are growing tired of extended wait times and spending $300 to address a simple illness or fill out a school participation form.

Consider today's system: (1) the patient becomes sick with a sore throat; (2) calls and makes an appointment at an over-booked, busy medical practice, or shows up randomly in a crowded wait room at a retail clinic with a handful of other infectious patients; (3) fills-out medical and legal and insurance and office forms, which then must be entered into the electronic medical record (EMR); (4) wait time in waiting room; (5) brought back to examination room, and more wait time for clinician to arrive; (5) actual clinical visit is often lengthened in greeting and other conversation, and interrupted by phone and EMR-typing requirements of clinician; (6) throat culture ordered, which requires additional lab wait; (7) drug treatment (90% of time scripts written), requiring prescription to be called-in to pharmacy; (8) patient leaves premise to go pick-up drug; (9) wait time at pharmacy. And the financial money flow is equally unattractive, laced with copays ($50-100 per office visit and $25-100 for prescriptions), enormous deductibles (in 2019, average deductible is over $8,000 per family), and healthcare inflation rates of 5-10%.

Historically, consumers were loyal to a single physician practice, and typically visited that practice to access primary care services. Today's consumers are less "connected" to any one individual physician, and thereby, far more wide-ranging in seeking immediate care. Hospital ER's still often serve as a "go to" primary care site. However, the hospital is very high cost. Minute clinics and urgent care clinics (sometimes located in retail drug stores) offer more competitive costs but are plagued with extensive wait times (in germ-infested waiting rooms), higher cost, and extensive paperwork. Home telemedicine visits offer little clinical information, provide little value, and typically result in a visit to a primary care provider (and eventually another stop at the local pharmacy). Consumers simply do not want the hassle of a delay in appointment availability, prolonged office wait times, inflated invoices, co-pays, deductibles for basic medical care.

Today's busy consumers seek a solution that provides fast, easy access to quality healthcare. The methods and systems disclosed herein provide such a solution, and overcome the problems and disadvantages discussed herein.

With a focus on what truly matters to the patient for most common maladies—that is, rapid clinical diagnosis & treatment—the methods and systems disclosed herein offer a more efficient and less expensive healthcare experience.

SUMMARY

The methods and systems disclosed herein can be described generally as Drive Through Medicine ("DTM"). DTM is a disruptive, "bricks & clicks" hybrid, health care delivery practice. Through a retail, drive-thru location with a suitable building structure/architecture, DIM will allow patients, to interact with a nurse practitioner, doctor, or other appropriate medical professional on site, and/or via a web-connected telemedicine robot, for a real time, telemedicine consult. Often, this will be accomplished without exiting one's car.

DTM will offer consumers fast, affordable and convenient medical care, addressing the common maladies of primary care medicine (sore throat, respiratory and sinus infections, ear aches, vaccinations, flu shots, cough/cold, skin rash, pink eye, urinary tract infection, school/camp/team medical forms, infected lacerations, etc.) in a cash-pay business transaction. The patient will also appreciate one-stop access to lab tests and blister packaged, ready-to-dispense generic pharmaceuticals available on-site. DTM will offer a medical visit that is faster (e.g., during the hours of 7 am to 8 pm, with a wait time measured in minutes), cheaper (e.g., basic visits cost under $50) and more convenient (e.g., prescription dispensed on site) than any Minute Clinic or urgent care center. And, in contrast to a home-based telemedicine visit, DTM will allow the medical professional to effectively diagnose and treat the patient, access patient vital signs, availability of instantaneous on-site lab tests, dispensing of generic drugs, and sale of OTC products.

DTM offers an innovative, first-to-market, drive-thru clinic, preferably featuring at least two clean and well-appointed patient privacy bays. Each bay will have a medical profession on site, and/or will feature an InTouch virtual care medical operating system robot. This device offers a high-resolution camera, television monitor, microphone, speaker, keyboard, stethoscope, blood pressure cuff thermometer, and otoscope all fully web-based, mounted on a robot-like device on wheels. This device is connected to the healthcare professional "in the cloud" and can readily be maneuvered adjacent to the vehicle. Upon arrival in the entry drive, an electronic "menu board" will allow the patient to register and provide preliminary symptoms. Then, the customer will be prompted to drive their vehicle directly into the private bay for an in person and/or telemedicine consult. When used, the telemedicine robot is situated adjacent to the vehicle, and DTM offers the customer a relatively short, e.g., 10-minute telemedicine visit with a healthcare professional who interacts with the patient. All data and professional interaction are recorded and uploaded to the patient's EMR. This collaboration is supported by an on-site, DTM medical representative, available for hands-on patient interaction and follow-up with the dispensing of prescribed generic pharmaceutical products (in blister-pack packaging) or sale of OTC products. The basic visit will cost a relatively inexpensive amount, e.g., $40; and preferably the entire visit, including generic prescription and basic lab tests, will usually cost under $100, payable at time of visit. Preferably, payments will be made electronically, and there will be no cash or controlled substances on the premises.

Through its convenient locations, no appointment scheduling, and a cash-and-carry payment transactions, DTM addresses the shortcomings in today's primary care medical system. Additionally, by leveraging leading artificial intelligence health platforms and on-line medical resources, DTM can provide a superior clinical experience, with no exposure to the germs and infections present in most medical offices.

Preferably, DTM comprises a highly visible, 4,000 square foot location, featuring at least two drive-through bays. DTM provides a business to consumer ("B2C") healthcare solution (addressing the unmet need among today's consumers), though DTM also has applicability in the business to business ("B2B") space, assisting employer health providers in their efforts to manage hypercholesteremia, diabetes, and hypertension (population health management).

BRIEF DESCRIPTION OF THE DRAWINGS

The drawing figures depict one or more implementations in accordance with the present teachings, by way of example only, not by way of limitation. In the drawing figures, like reference numerals refer to the same or similar elements.

FIG. 2 is an overhead perspective view of the DTM building of FIG. 1.

DETAILED DESCRIPTION

The following description refers to numerous specific details which are set forth by way of examples to provide a thorough understanding of the relevant method(s) and system(s) disclosed herein. It should be apparent to those skilled in the art that the present disclosure may be practiced without such details. In other instances, well known methods, procedures, components, instruments, implements and/or devices have been described at a relatively high-level, without detail, in order to avoid unnecessarily obscuring aspects of the present disclosure.

FIGS. 1-21 illustrate and described in more detail one or more embodiments of the DIM methods, systems and building structures/architecture.

Figure 1:
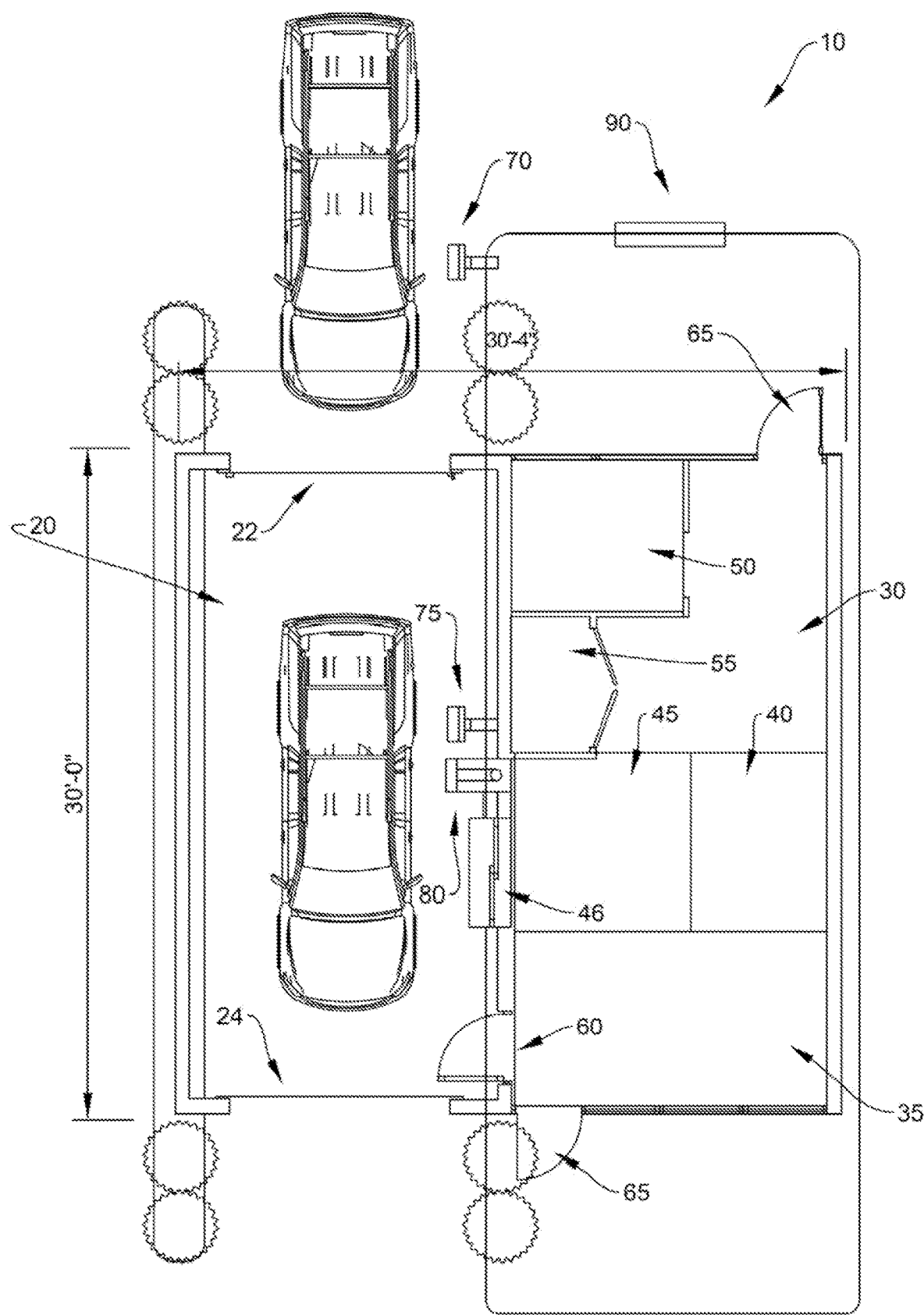
FIG. 1 is a schematic illustration of a DTM building of the present disclosure.
Figure 3C:
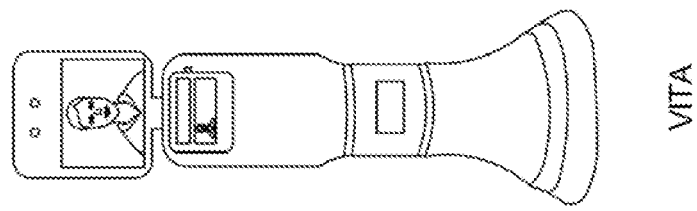
FIG. 3C is an illustration of another alternate embodiment of a telemedicine device.
Figure 3B:
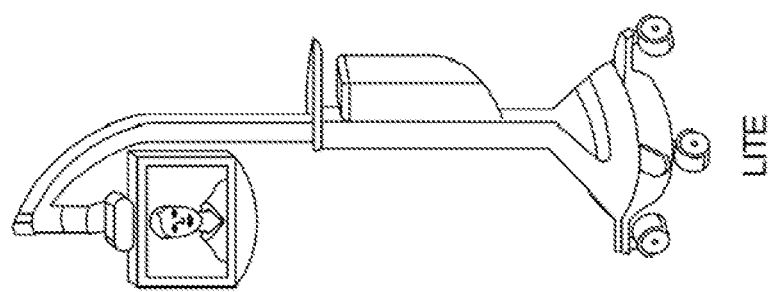
FIG. 3B is an illustration of an alternate embodiment of a telemedicine device.
Figure 3A:
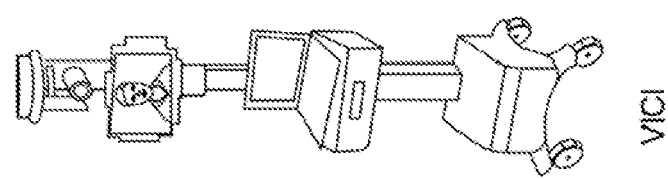
FIG. 3A is an illustration of one embodiment of a telemedicine device.

FIG. 1 is a schematic diagram of an exemplary embodiment of a building 10 for the DIM systems and methods disclosed herein. FIG. 2 illustrates an overhead perspective view of the building 10. This building 10 creates a new destination for DTM. The building 10 comprises a convenient, quick service, medical services center that does not require a user to leave their car for most services. The building 10 includes one or more consult bays 20 that allow users to drive in and engage a healthcare technician in privacy. The bay has a bay entrance door 22 and a bay exit door 24. The building 10 also includes at least one service area 30 which includes one or more of the following areas: at least one exam room 35, at least one restroom 40, at least one work space 45, at least one office space 50, at least one storage space 55, at least one interior entrance/exit 60 and at least one exterior entrance/exit 65.

Additionally, the building 10 includes at least one user interface 70, which may be used as a check in-station located outside the bay 20 to allow one user to check in while another user is in the bay 20. The building 10 may have a second user interface 75 which is inside the bay 20. The second user interface 75 may be used as a check in station in addition to or instead or the outside check-in station. User interfaces 70 and 75 comprise suitable hardware and software to allow the user to interact with the DIM system and enter user information by way of, for example, a touchscreen and/or other suitable device(s) such as an interactive voice recognition system, keyboard and mouse, etc.

The DTM site is preferably staffed by one or two workers per consult bay. First, a medical professional such a physician or physician's assistant (PA) will interact with the patient, and run various tests, screenings or lab work, and administer any shots or vaccinations, medications or medical supplies. Second, a technician or medical assistant (MA) will assist the PA as needed, and can fill and hand deliver medication while the PA is with the patient.

Figure 4:
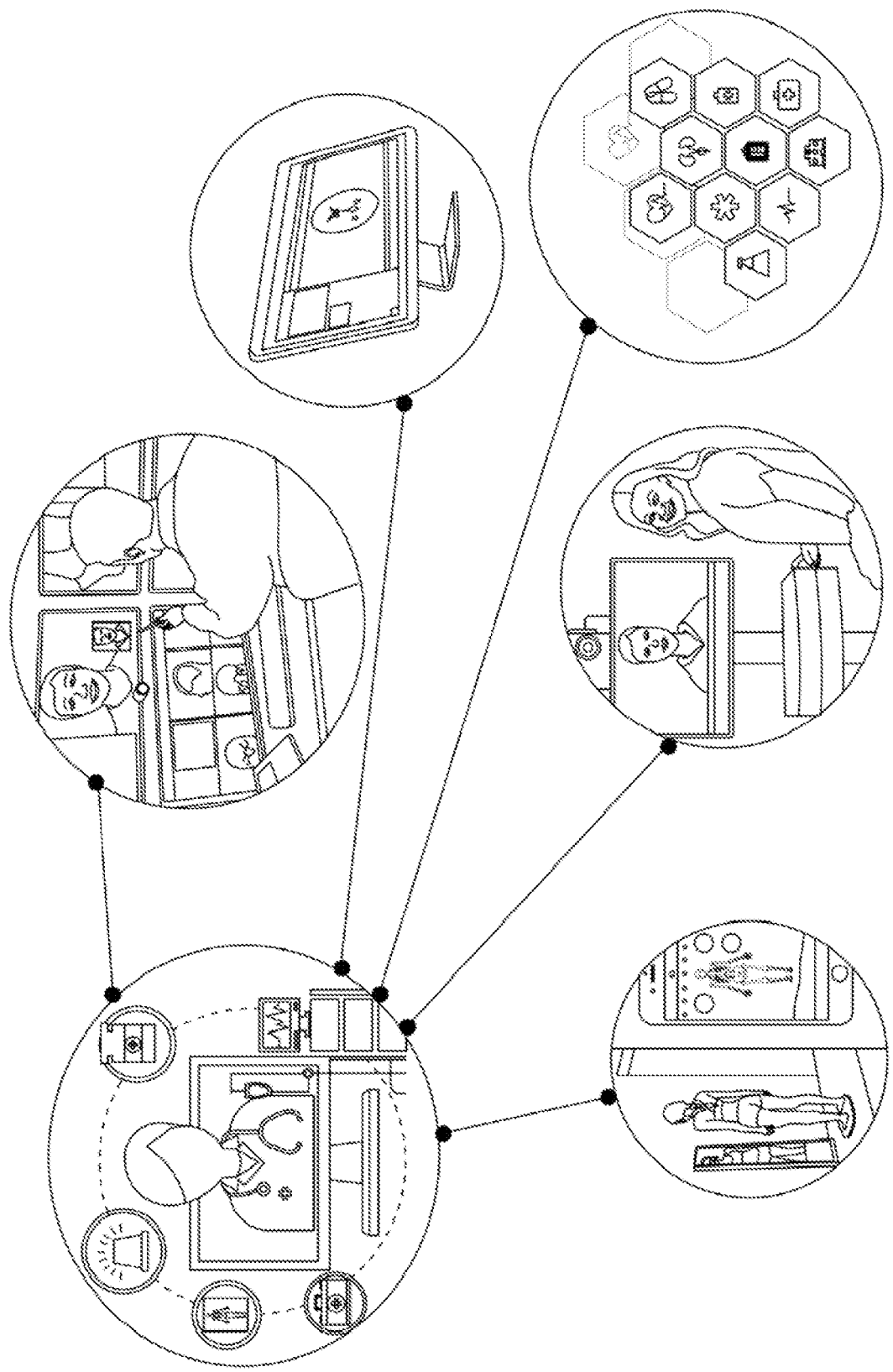
FIG. 4 is a diagram of a number of technologies used for telemedicine.

Also, preferably located in each bay 20 is a telemedicine system 80 which allows the user to have a visit or consultation with a virtual doctor or other medical professional, remotely, if necessary or desired. However, where the PA can handle the patient's needs, such a telemedicine consult may not be necessary. The telemedicine system 80 includes hardware and software which allows the user to interact with the medical professional remotely. For example, the telemedicine system 80 may be one of the telemedicine devices pictured in FIG. 3A (VICI system), FIG. 3B (LITE system) or FIG. 3C (VITA system) manufactured by InTouch Health of Santa Barbara, California. FIG. 4 illustrates additional telemedicine technologies that may be used in connection with the DTM methods and systems disclosed herein.

The DTM building may also be equipped with additional medical equipment as desired to fulfill any particular patient need. For example, a particular DTM building may specialize in radiology services and have a x-ray machine, CT scan machine, MRI machine, etc. It is foreseen that the DTM building may provide a wide range of services to patients, or specialize in particular services. One example of specialized services would be testing services. These services are available to the general population and no referral is necessary.

In use, the DTM building, system and method preferably include the steps of self-check-in through an interactive screen at user interface 70 and/or though a website or mobile app, which preferably utilizes a cloud based software system for the DTM services. This self-check-in process includes a series of questions to determine the medical needs of a user. The user will then drive their car forward to enter the privacy bay 20. The PA and/or MA in work space 45 can interact with the user through a service window 46 or other suitable opening, or can enter the bay to directly interact with the patient as needed. While inside the privacy bay, the user will visit or consult with the medical professional on site, and/or can have a telemedicine consult remotely. This visit will preferably last less than 10 minutes. After this visit, the technician will issue the user a medical blister pack based on doctor prescription. The medical blister pack may contain medicine and/or medical supplies.

Figure 5:
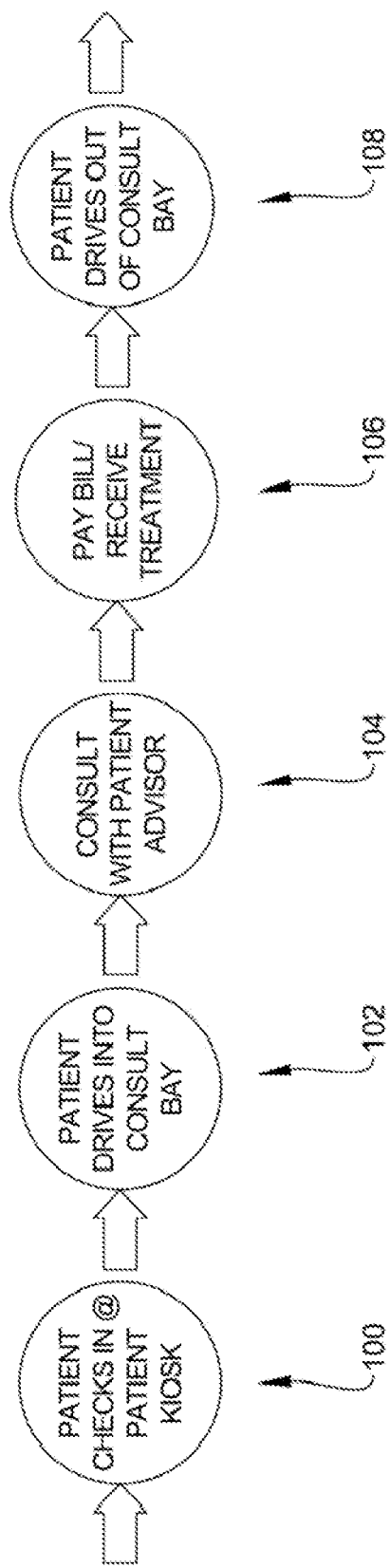
FIG. 5 is a flow chart of the DTM method of the present disclosure.

FIG. 5 illustrates a basic flow chart of the DTM process. In Step 100, the patient checks in at the patient kiosk. Check-in at the kiosk ensures every car is following a similar cadence/timing. This step may also include the use of a website or mobile app through which the patient can answer intake questions remotely, before driving to the DTM site, or while waiting in line at the DTM site. After a patient submits answers to intake questions, a text or email confirmation can be sent to the patient. If patient is experiencing chest pain or other serious symptoms, a call for an ambulance can be made to 911. In Step 102, the patient drives into one of the consult bays. The patient's car is turned off, and the garage door closes. In Step 104, the patient consults with a patient advisor. A certified nursing assistant confirms the patient's intake questions/answers and takes the patient's vitals. Consultation and care then take place. The DTM clinic has point of care prescriptions, labs, and vaccines. In Step 106, the patient pays the bill and receives treatment. The patient pays for the consultation via credit card or insurance. The patient then receives two documents (via print, email or both): a care plan and a receipt. In Step 108, the patient drives out of consult bay. The DTM system will also send a follow-up email to the patient 24 hours after their DTM visit.

The patient intake process which preferably is done through a website or mobile app prior to arriving at the check-in kiosk, involves three steps. First, the patient will schedule an appointment. To schedule an appointment, the user will select a DTM clinic location. The user will the select the type of appointment, e.g., general check-up, specific acute condition, immunization, lab test, or other. The user will then select either Appointment Time Slot or "Drive-in." Next, the user will answer the intake questions as follows: 1. First Name, 2. Last Name, 3. Home Address, 4. Date of Birth, 5. Male/Female, 6. Mobile Phone Number, 7. Email, 8. Insurance (insurance carrier, plan name, group ID, and member ID), 9. Open Text Box for Chief Complaint (sore throat, bad cough, etc.), 10. Drug Allergies, 11. Current Medications, 12. Primary Care Provider (if patient has one), 13. Emergency Contact Name, 14. Emergency Contact Phone Number, and Upload Photo of the patient to confirm identity. Finally, the patient will e-sign or upload an Informed Consent Form and Required Compliance Forms.

The DTM building will preferably be open twelve hours a day, and service approximately eighty patients per day. A waiting time indicator 90 may be provided near the check-in station 70 to inform users in line of the wait time. One or two employees per consult bay maximum, as well as the appropriate technology described herein, are needed on premises to provide the DTM service. For the user, 98% of each visit will take place in their car, while the exam room 35 is provided for physical inquiries. For example, the patient may exit their car and use the exam room's restroom to provide a urine sample.

The following factors will drive down consultation time: 1. Pre-visit intake on cellphone or PC (15-20 questions); 2. Sub acuity of illness (common maladies responsible for 80% primary care); 3. EMR charting speed; 4. Use of diagnosis templates; 5. a medical assistant that can fill and deliver medication to patient as PA works with patient; 6. a medical assistant that can quickly move patient out of bay into designated test waiting stall/parking spaces for pos/neg result.

The following are examples of estimated times for various visits of common clinical diagnoses (in minutes/seconds):
1) Acute Pharyngitis (Sore Throat)
   Time: 10:07—If patient leaves bay and parks in test waiting stall for pos/neg result from rapid throat test swab
   Time: 15:07—If patient remains in the bay waiting for result
   No added wait for prescription drug because medical assistant (MA) will be filling and hand delivering the drug for acute pharyngitis.
2) Wellness Screening Vitals and Routine Health Labs
   Time: 7:36—Includes blood draw
3) UTI (Urinary Tract Infection)
   Time: 12:56—Includes obtaining urine specimen from patient and running urine dipstick
   No added wait for prescription drug as MA will be filling and hand delivering the antibiotic for UTI.
4) Covid Exposure
   Time: 9:57—If patient leaves bay and parks in test waiting stall for pos/neg result
   Time: 19:57—If patient remains in the bay waiting for result
5) Acute Influenza—Includes three rapid throat swabs (FLU, Covid, and Strep)
   Time: 9:44—If patient leaves bay and parks in test waiting stall for pos/neg result
   Time: 19:44—If patients remains in the bay waiting for results.
   No added wait for prescription drug as MA will be filling and hand delivering the anti-flu medicine and possibly a second medicine antibiotic to cover bacterial URI.
6) Acute Back Pain
   Time: 9:36
   No added wait for prescription drug as MA will be filling and hand delivering muscle relaxant medicine and 2nd medicine NSAID.

7) Acute Gastroenterids (Nausea and Diarrhea)
   Time: 9:39
   No added wait for prescription drug as MA will be filling and hand delivering antidiarrheal medicine and medicine 2nd medicine anti-nausea medicine.
8) Acute Hives (Itchy Rash)
   Time: 9:34
   No added wait for prescription drug as MA will be filling and hand delivering anti-itch medicine and medicine 2nd medicine anti-itch cream.

Figure 6:
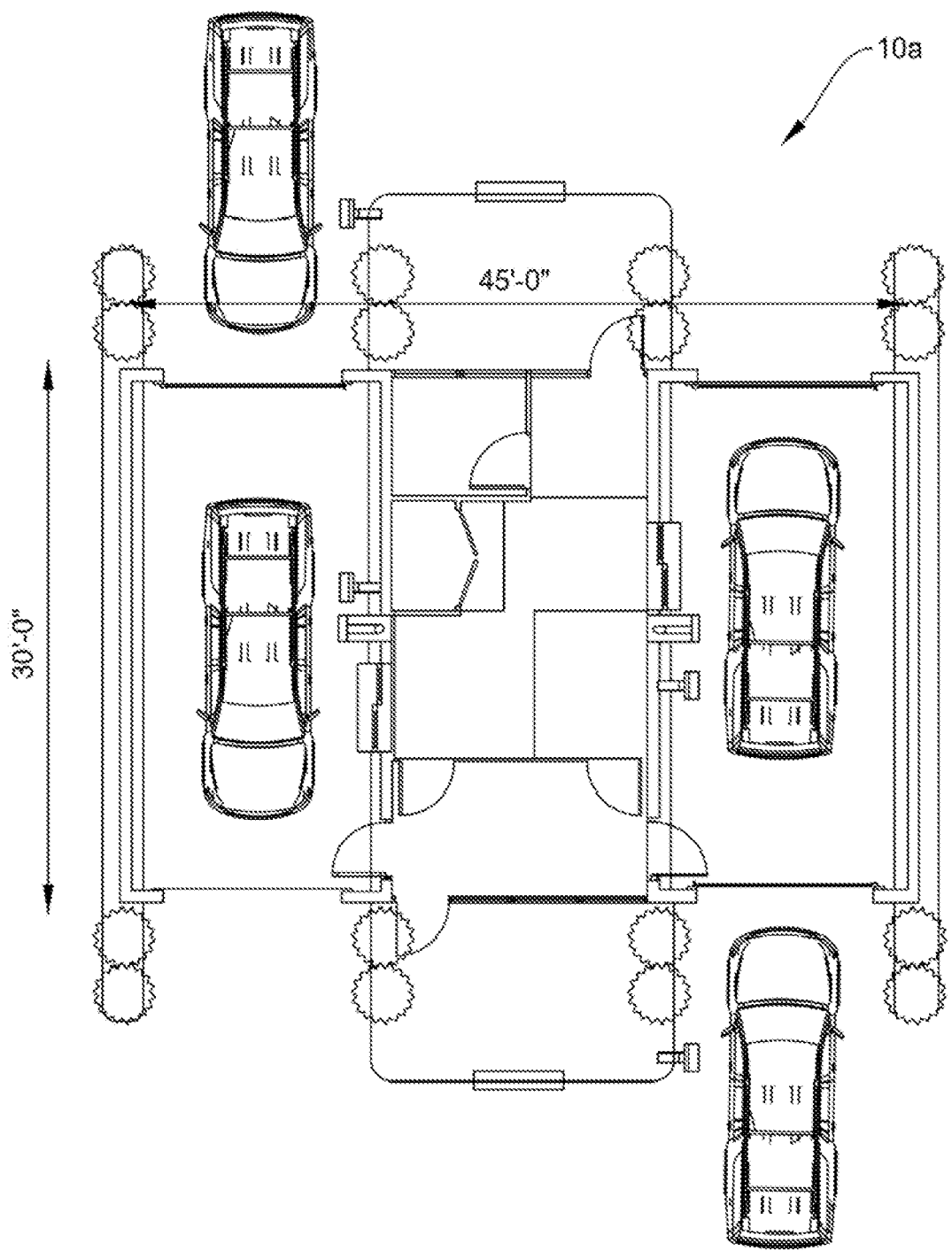
FIG. 6 is a schematic illustration of an alternate embodiment of a DTM building of the present disclosure having two consult bays.

FIG. 6 is a schematic diagram of an alternate embodiment of a building 10a for the DTM systems and methods disclosed herein. The building 10a includes two consult bays that allow two users at the same time to drive in and engage a respective healthcare technician in privacy. As such twice as many patients may be serviced each day. Each bay has a bay entrance door and a bay exit door. The building 10a also includes at least one service area which includes one or more of the following areas: at least one exam room, at least one restroom, two work spaces, each with a service window, at least one office space, at least one storage space, two interior entrances/exits, and two exterior entrance/exit. While one exam room and one restroom are illustrated as being shared by the two bays, it should be understood that each bay may have its own exam room and restroom. Additionally, the building 10a includes two user interfaces, each which may be used as a check in-station located outside a respective bay to each allow one user to check on while another user is in the respective bay. The building 10a may have a second user interface inside each bay. Also, preferably located in each bay is a telemedicine system.

Figure 7:
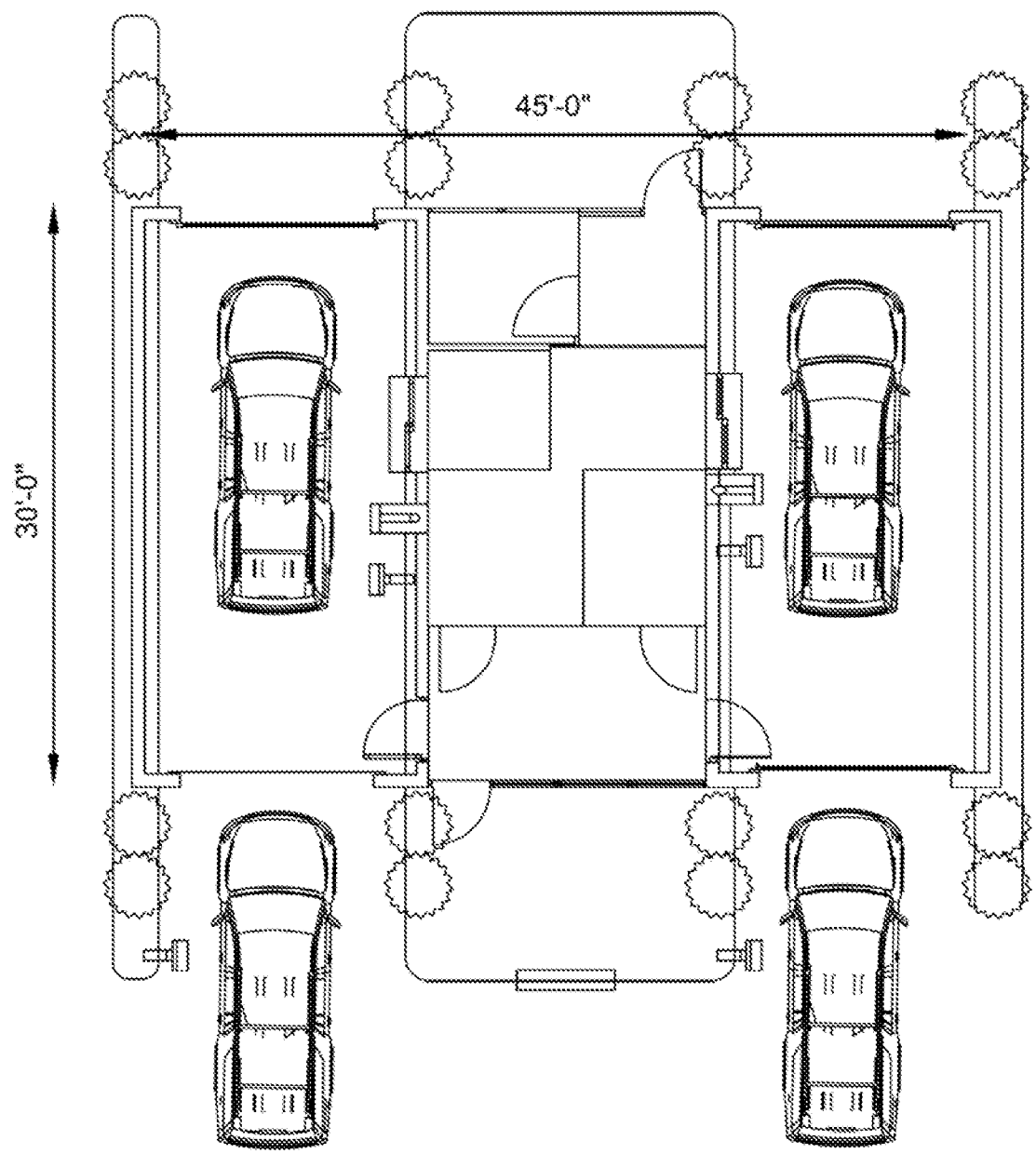
FIG. 7 is a schematic illustration of alternate embodiment of the DTM building of FIG. 6.

In the embodiment of FIG. 6, traffic flows into the bays in opposite directions. However, it is foreseen that traffic can flow into the bays in the same direction, as illustrated in FIG. 7.

Figure 8:
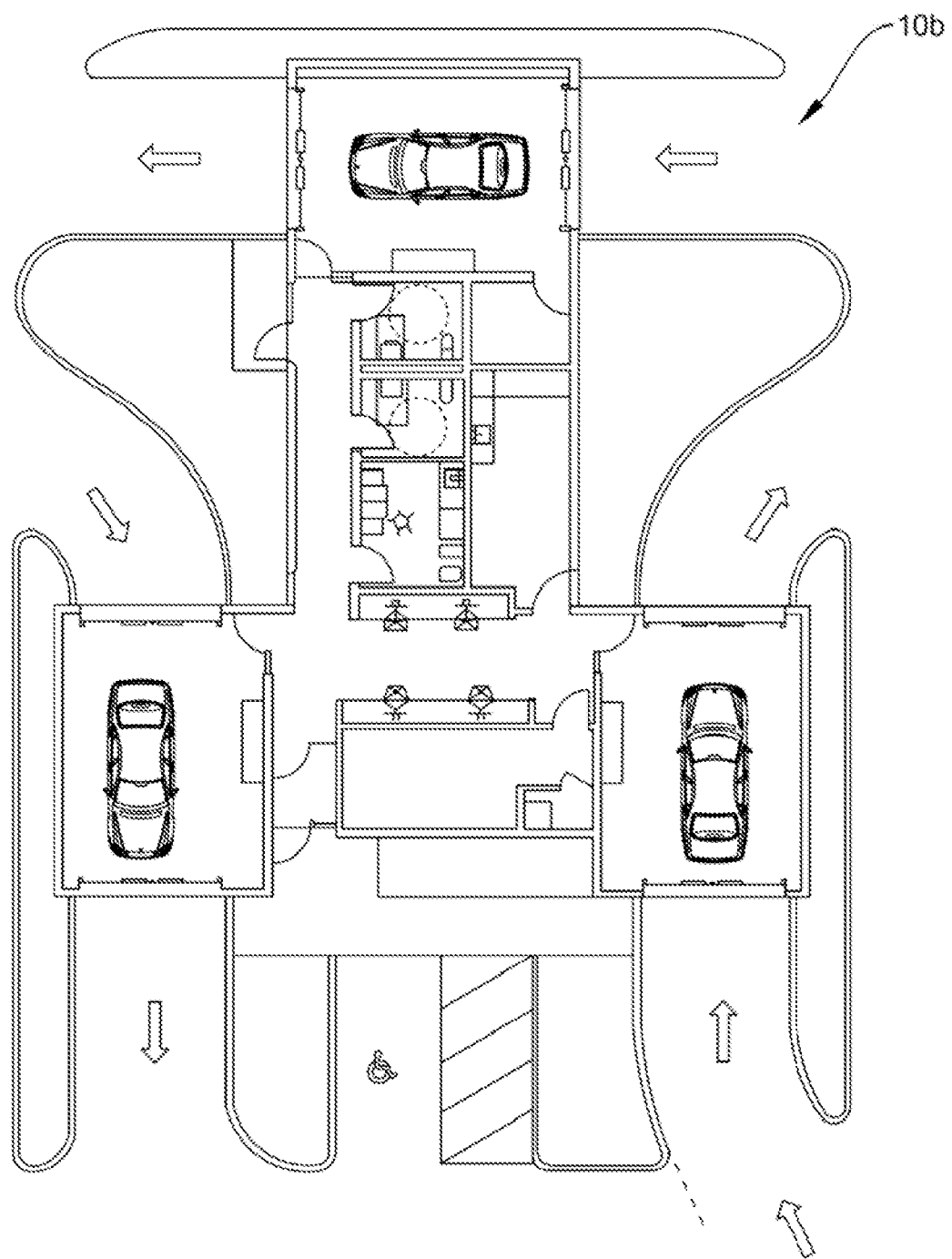
FIG. 8 is a schematic illustration of an alternate embodiment of a DTM building of the present disclosure having three consult bays.
Figure 9:
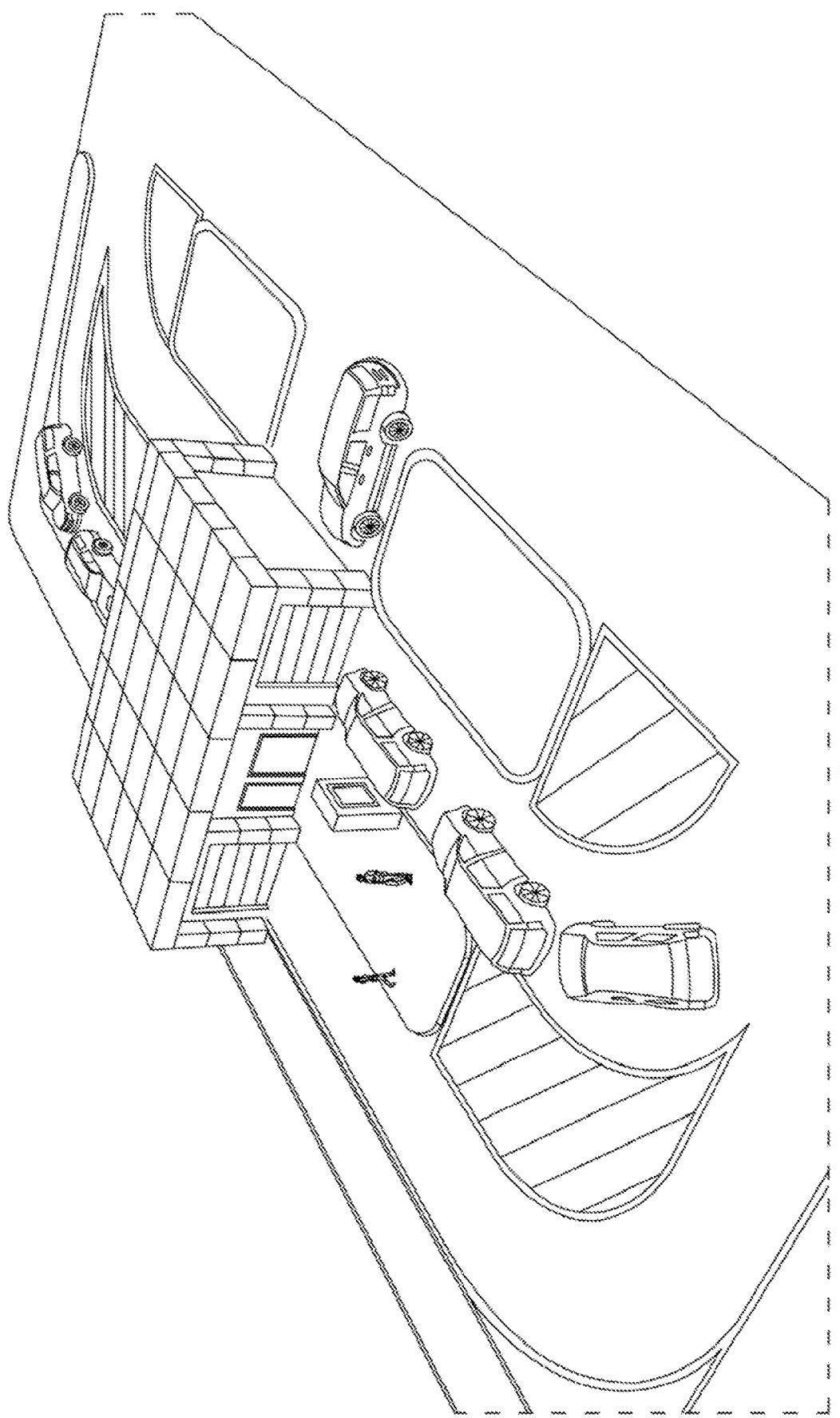
FIG. 9 is an overhead perspective view of the DTM building of FIG. 6.
Figure 10:
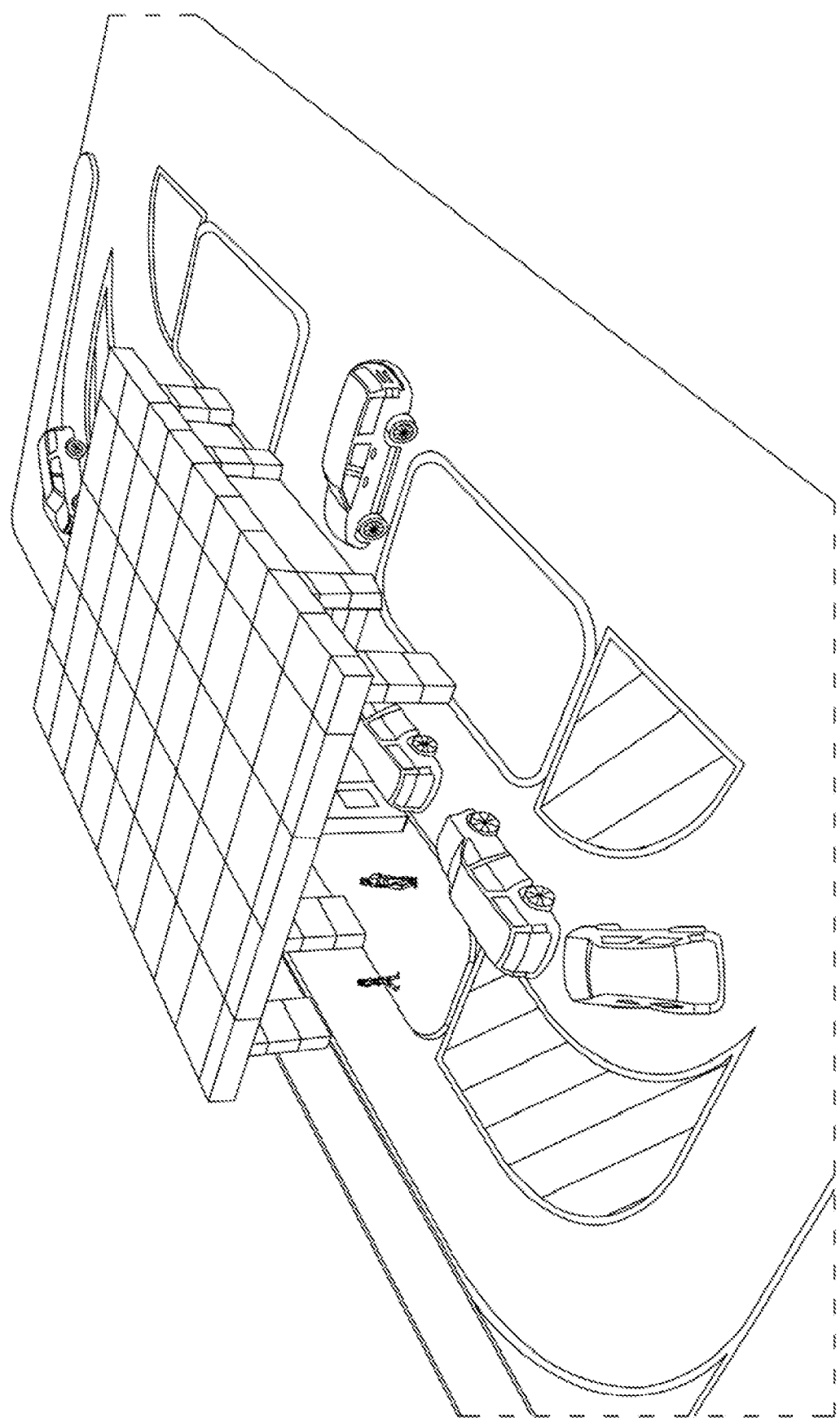
FIG. 10 is an overhead perspective view of an alternate embodiment of the DTM building of FIG. 6.
Figure 11:
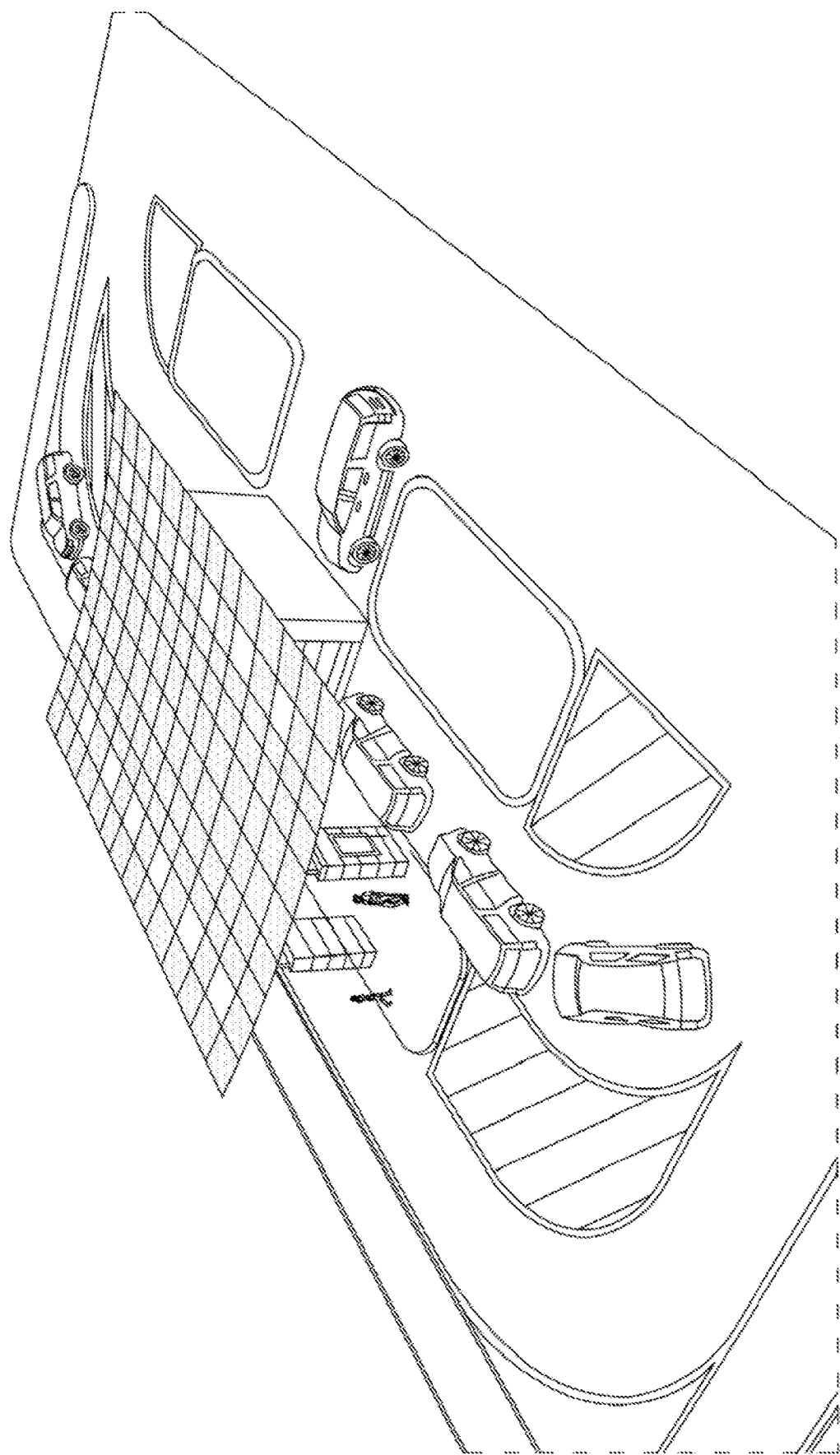
FIG. 11 is an overhead perspective view of another alternate embodiment the DTM building of FIG. 6.
Figure 12:
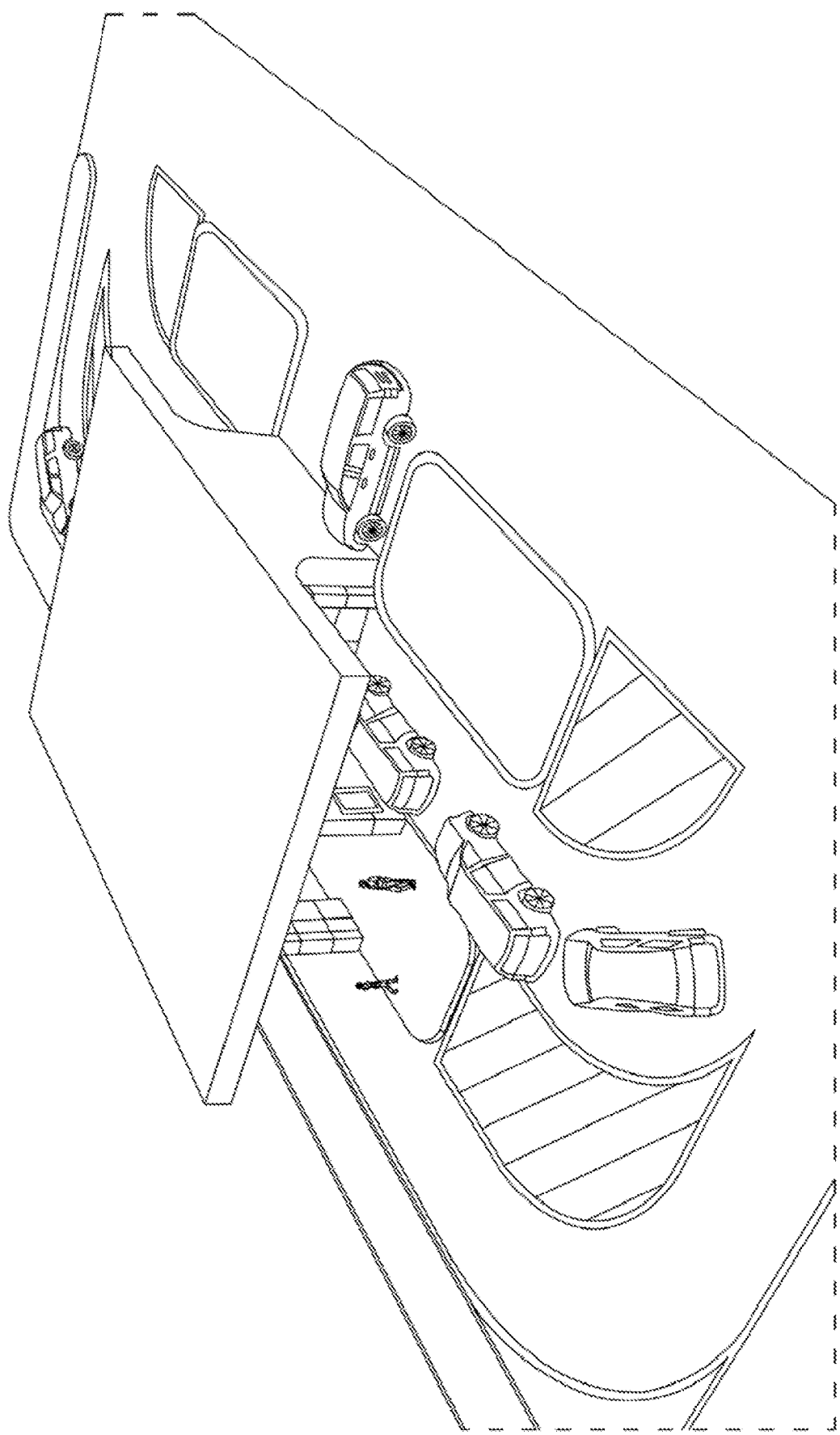
FIG. 12 is an overhead perspective view a further alternate embodiment of the DTM building of FIG. 6.
Figure 13:
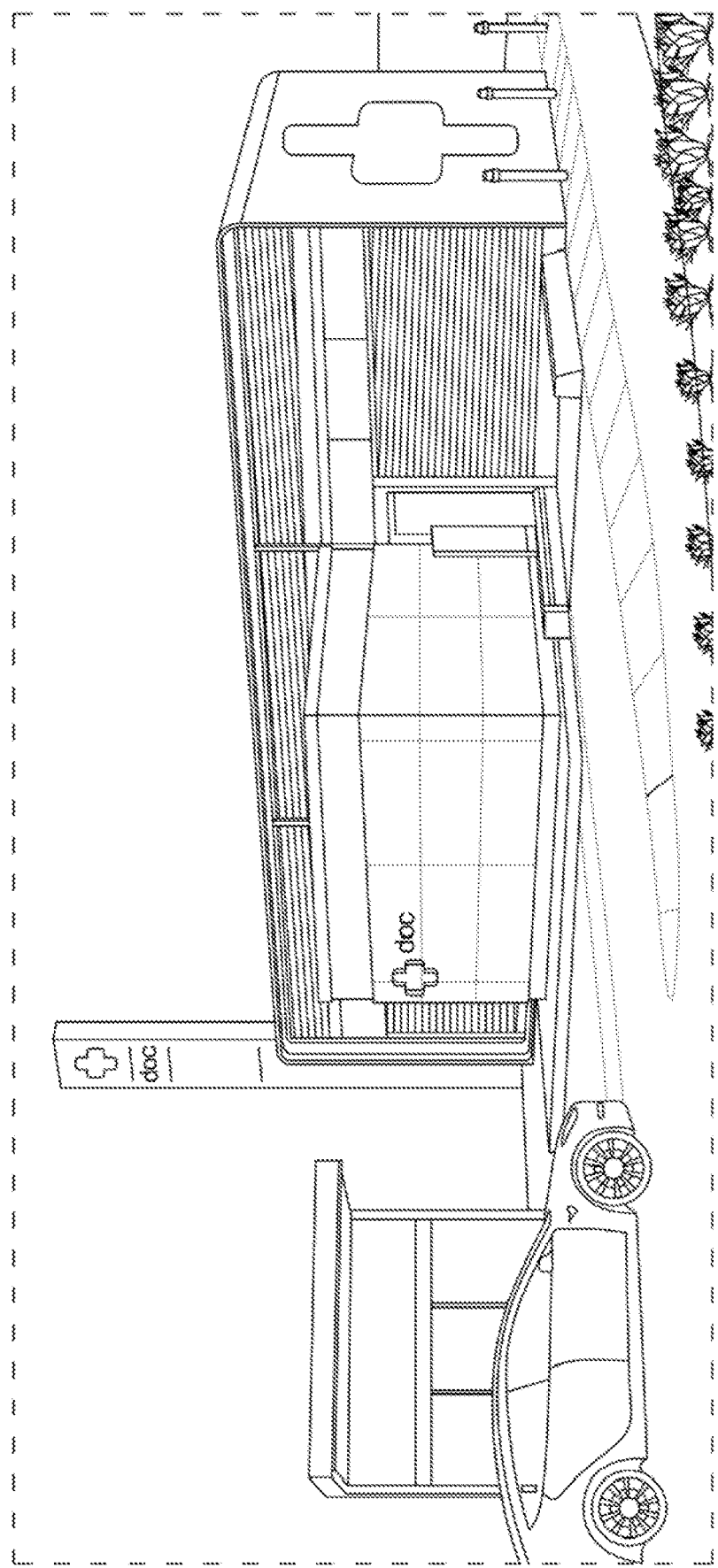
FIG. 13 is a perspective view an additional alternate embodiment of the DTM building of FIG. 6.

FIG. 8 is a schematic diagram of an alternate embodiment of a building 10b for the DTM systems and methods disclosed herein. The building 10b includes three consult bays that allow three users at the same time to drive in and engage a respective healthcare technician in privacy. As such three times as many patients may be serviced each day. Each bay has a bay entrance door and a bay exit door. The building 10b also includes at least one service area which includes one or more of the following areas: at least one exam room, at least one restroom, multiple work spaces, at least one office space or break room, at least one storage space, three interior entrances/exits to the bays, and at least one exterior entrance/exit. While one exam room and two restroom are illustrated as being shared by the three bays, it should be understood that each bay may have its own exam room and restroom. Also, preferably located in each bay is a telemedicine system.

The building structure preferably has a modern and eye catching design, using contemporary materials like glass in metal for the exterior finishes for an appealing facade that will stand out and be unique. Exemplary building designs of the two bay embodiment of FIG. 6 are illustrated in the overhead perspective views FIGS. 9-13. It is foreseen that these designs can be used for the embodiment of FIG. 7 as well.

Figure 14:
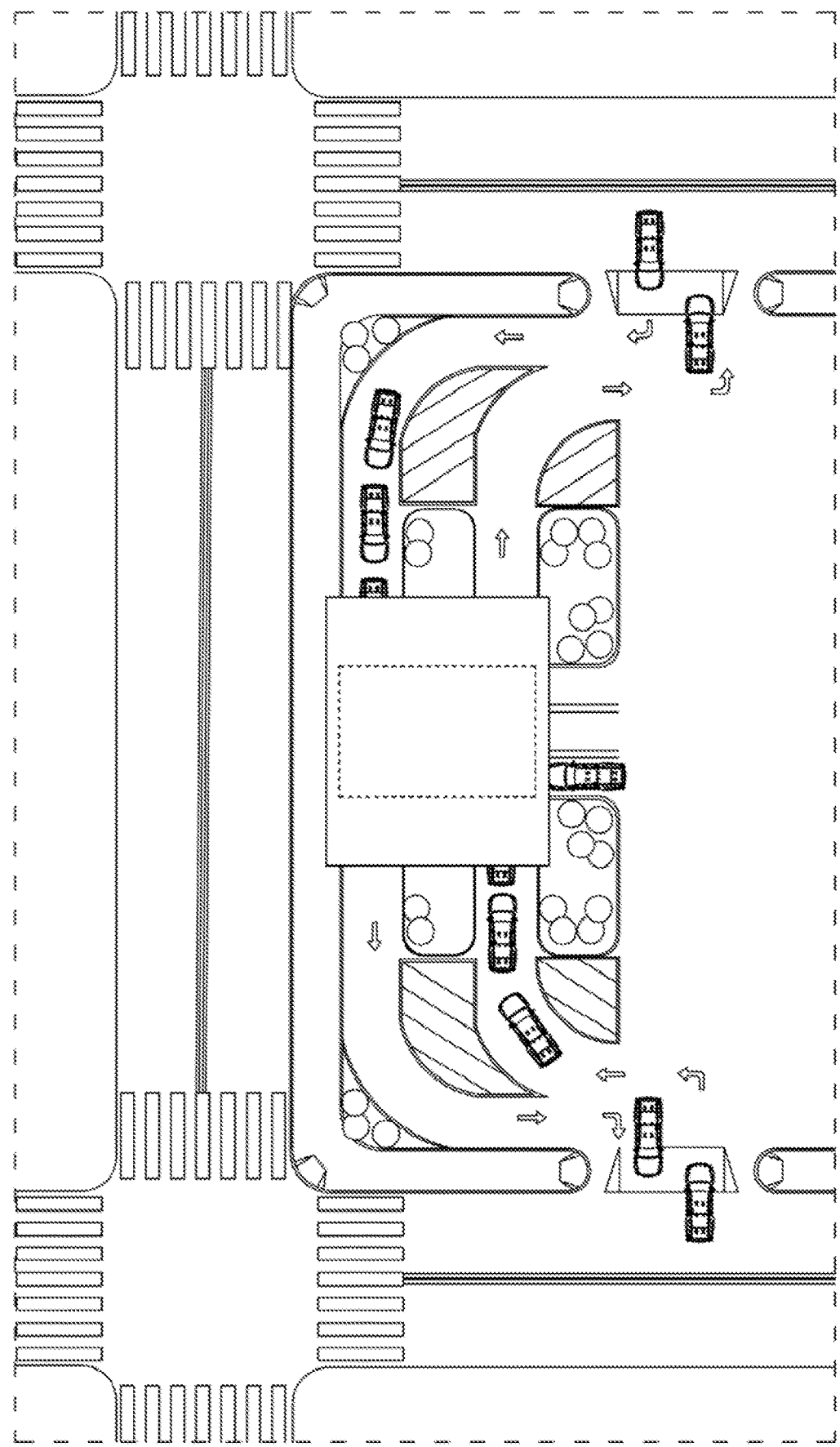
FIG. 14 is a schematic diagram of one embodiment of traffic flow for the DTM building of FIG. 6.
Figure 15:
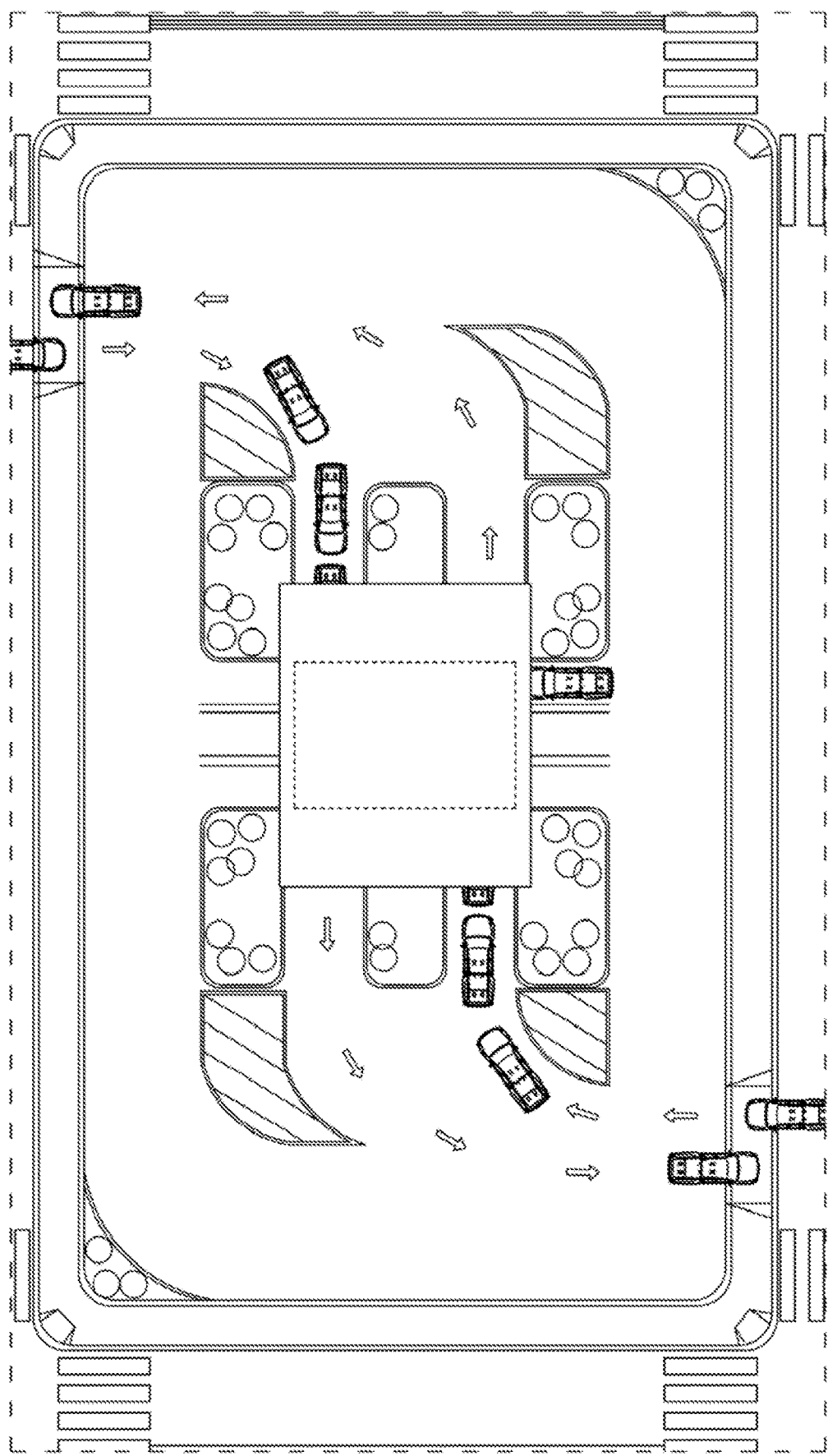
FIG. 15 is a schematic diagram of an alternate embodiment of traffic flow for the DTM building of FIG. 6.
Figure 16:
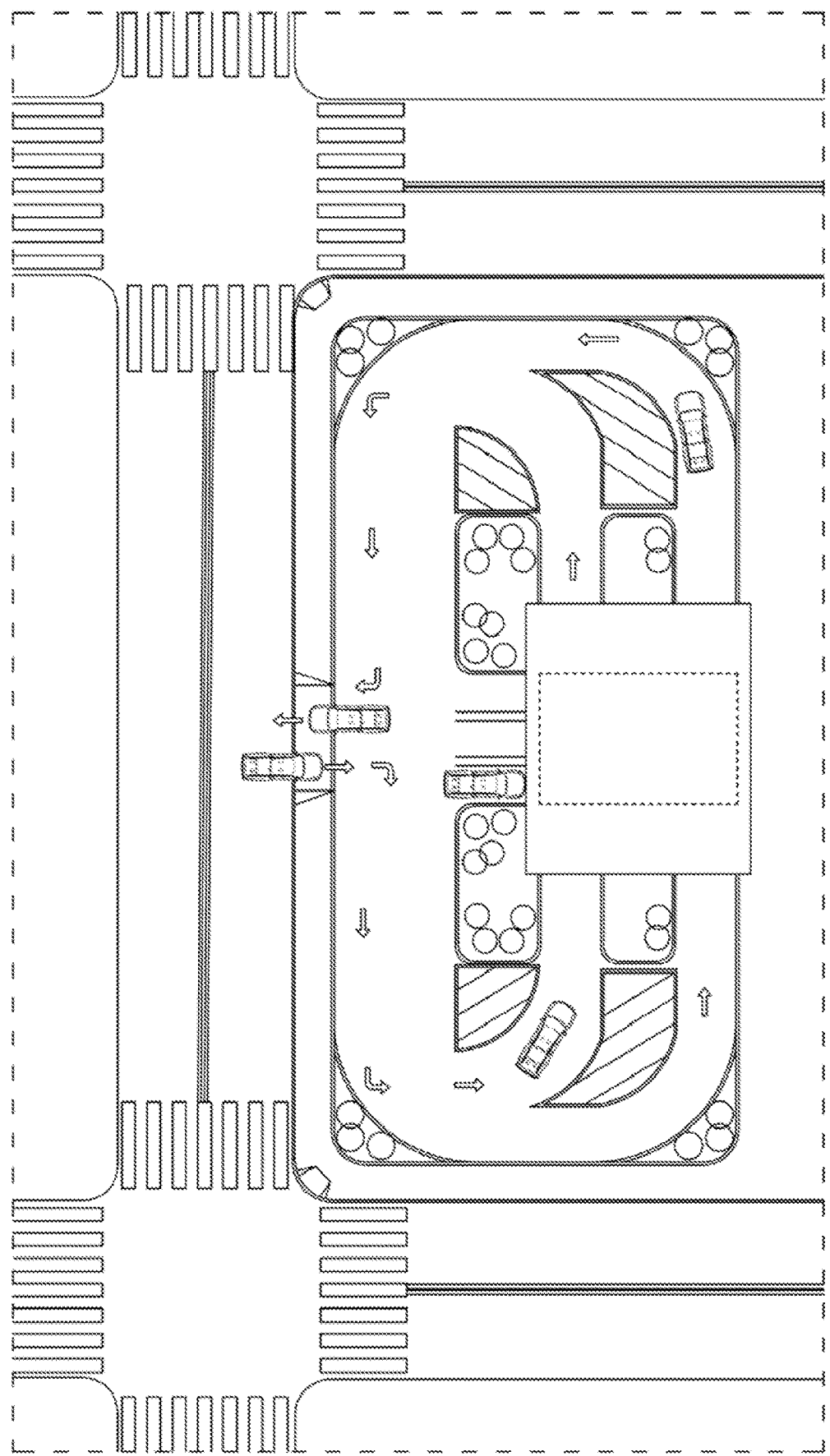
FIG. 16 is a schematic diagram of one embodiment of traffic flow for the DTM building of FIG. 7.

FIGS. 14-15 are schematic diagrams of the traffic flow of the embodiment of FIG. 6. In FIG. 14, traffic enters off the street from respective ends of the bays, proceeds through the respective bays, and then exits to the street at opposite respective ends of the bays. In FIG. 15, traffic enters off the street from respective sides of the bays, turns and proceeds through the respective bays, and then turns and exits to the street at opposite respective sides of the bays. FIG. 16 is a schematic diagram of the traffic flow of the embodiment of FIG. 7. In FIG. 16, traffic enters off the street from one side of the bays, proceeds around to and through the respective bays, and then proceeds around to and exits to the same street, in a circular fashion.

Figure 17:
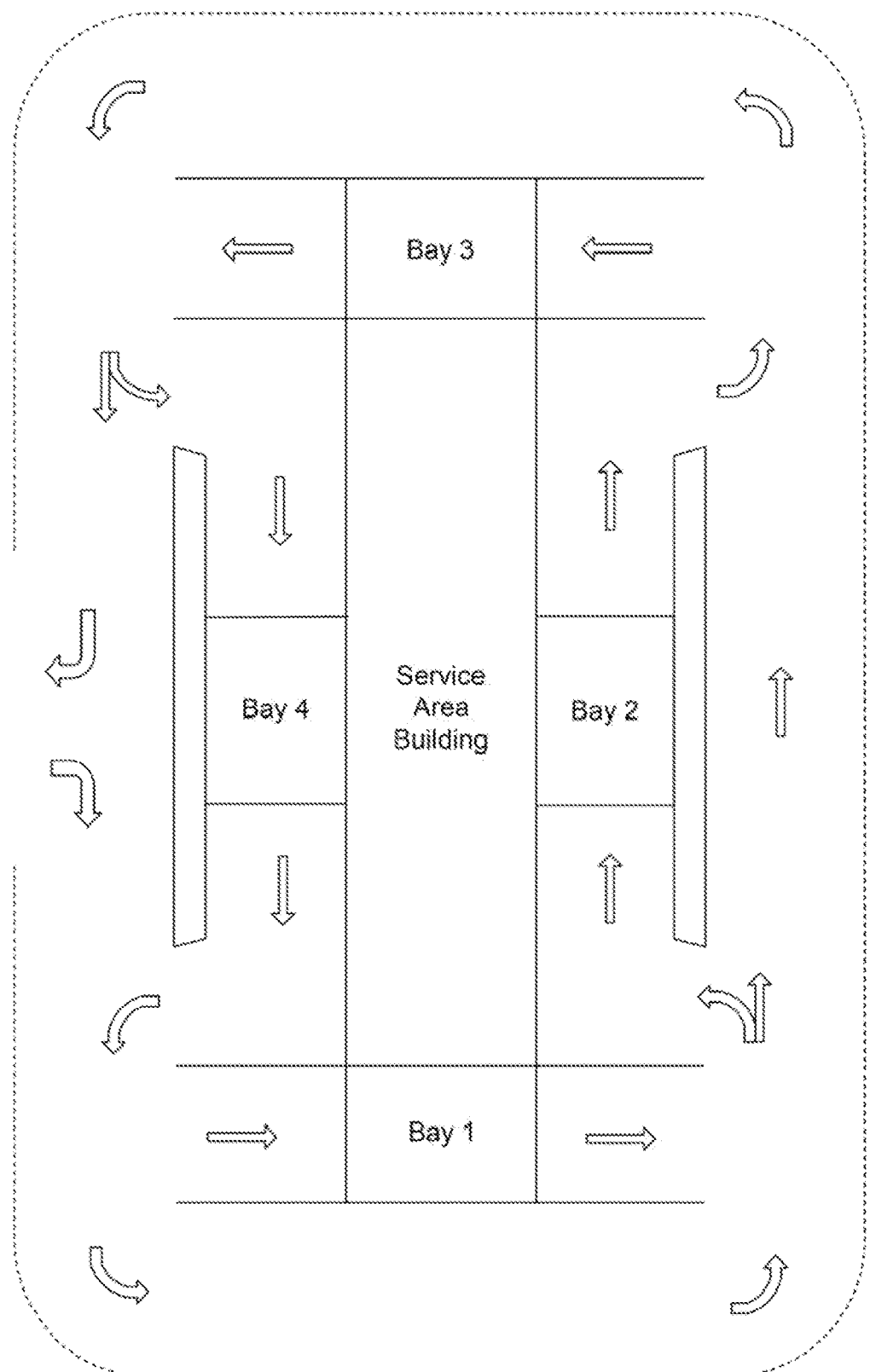
FIG. 17 is a schematic illustration of an alternate embodiment of a DTM building of the present disclosure having four consult bays.
Figure 18:
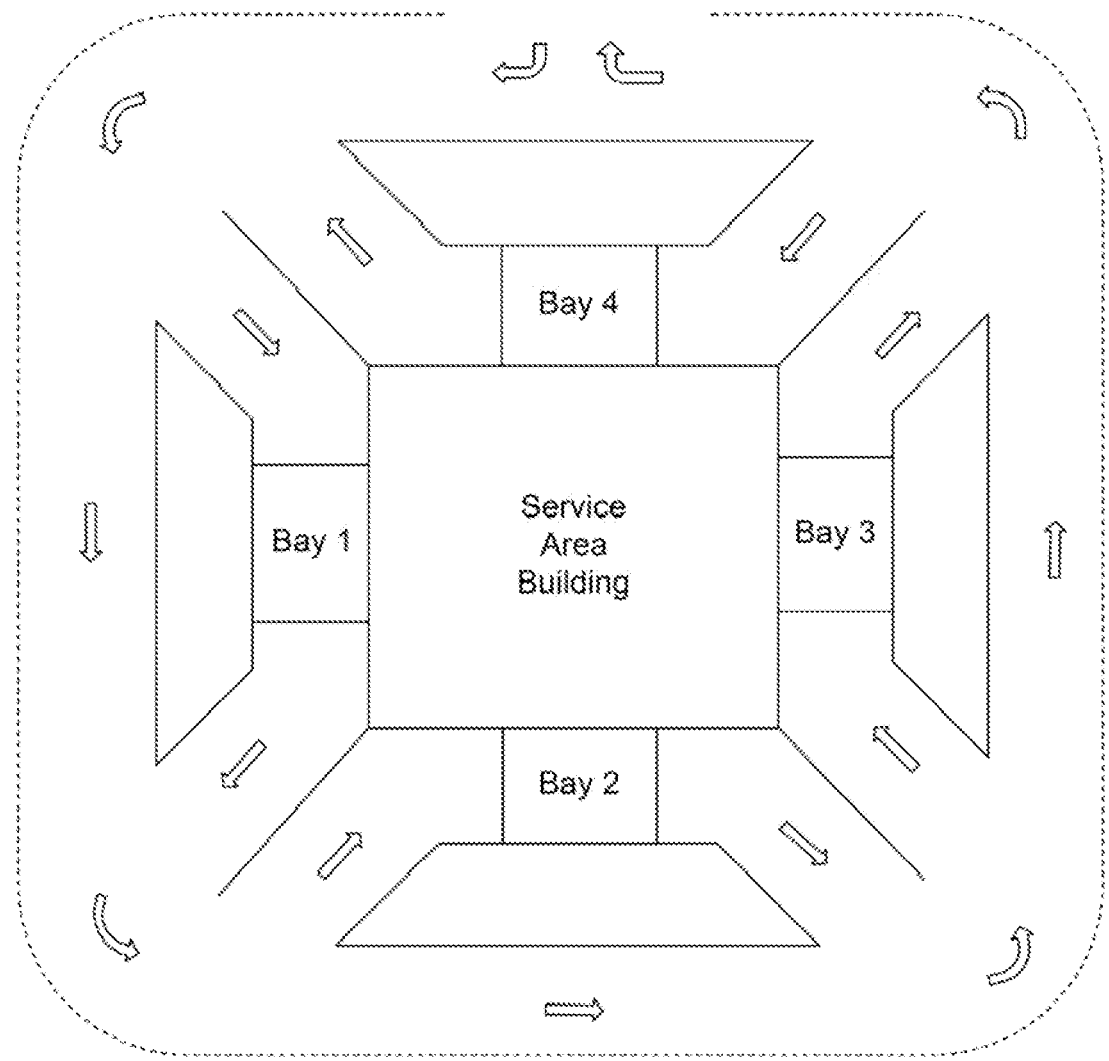
FIG. 18 is a schematic illustration of another alternate embodiment of a DTM building of the present disclosure having four consult bays.

FIGS. 17-21 illustrate alternate embodiments of the DTM building. Arrows indicate traffic flow. In FIG. 17, a rectangular service area building has four consult bays attached thereto. In FIG. 18, a square service area building has four consult bays attached thereto. In the embodiments of FIGS. 17 and 18, the paths of cars entering and exiting the bays do not intersect.

Figure 19:
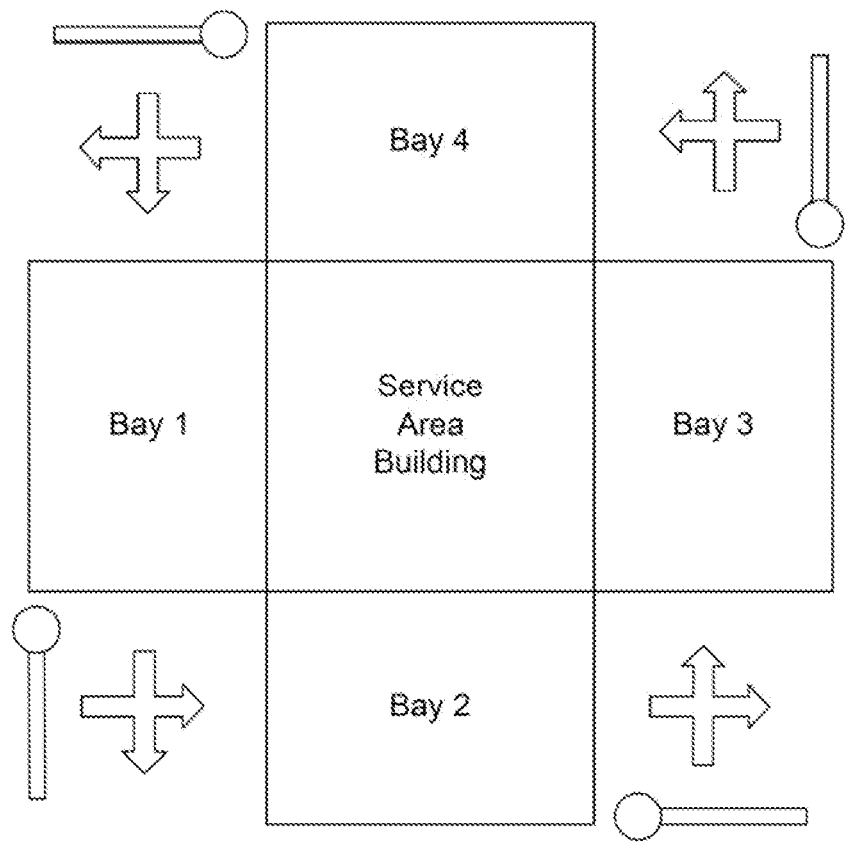
FIG. 19 is a schematic illustration of an additional embodiment of a DTM building of the present disclosure having four consult bays and traffic gates.

In FIG. 19, a square service area building has four consult bays attached thereto, wherein the paths of cars entering and exiting the bays do intersect. As such, traffic gates are provided to regulate the flow of traffic though the intersections. The traffic gates can lift up like toll booth gates, or could swing in front of the a exit door of a bay to block exit from that bay while a car enters an adjacent bay. For example, in FIG. 19, the gate regulating flow into bay 1 can swing to block the exit of bay 4 while a car enters bay 1. Alternatively, the entrance and exit doors can be in wired or wireless communication and synced so that while an entrance door in one bay is open, the exit door in another bay will be prevented from opening. For example, in FIG. 19, the entrance door for bay 1 is open, the exit door for bay will be closed and cannot be opened. Similarly, entrance doors can be locked when exit doors are open.

Figure 20:
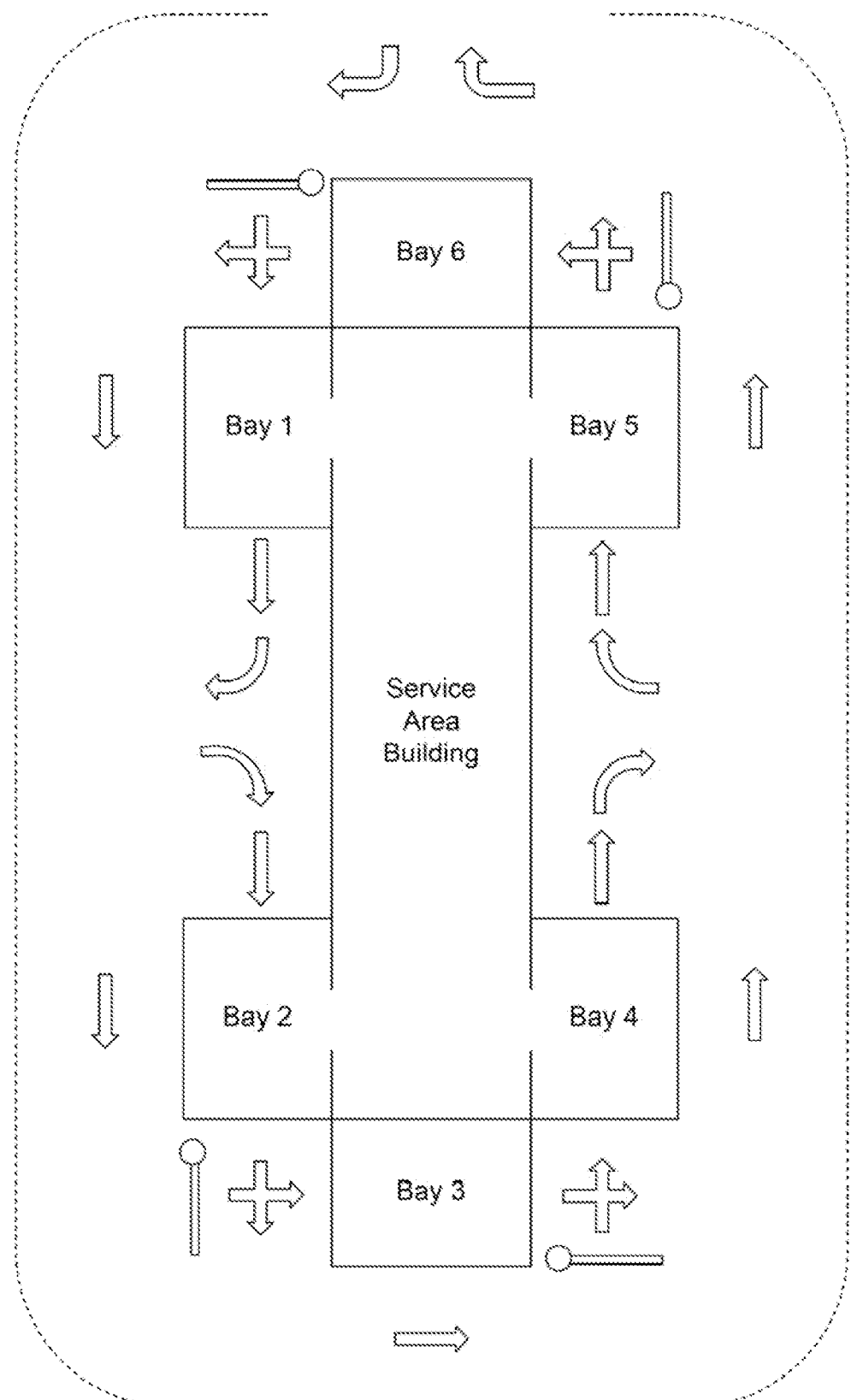
FIG. 20 is a schematic illustration of an alternate embodiment of a DTM building of the present disclosure having six consult bays.
Figure 21:
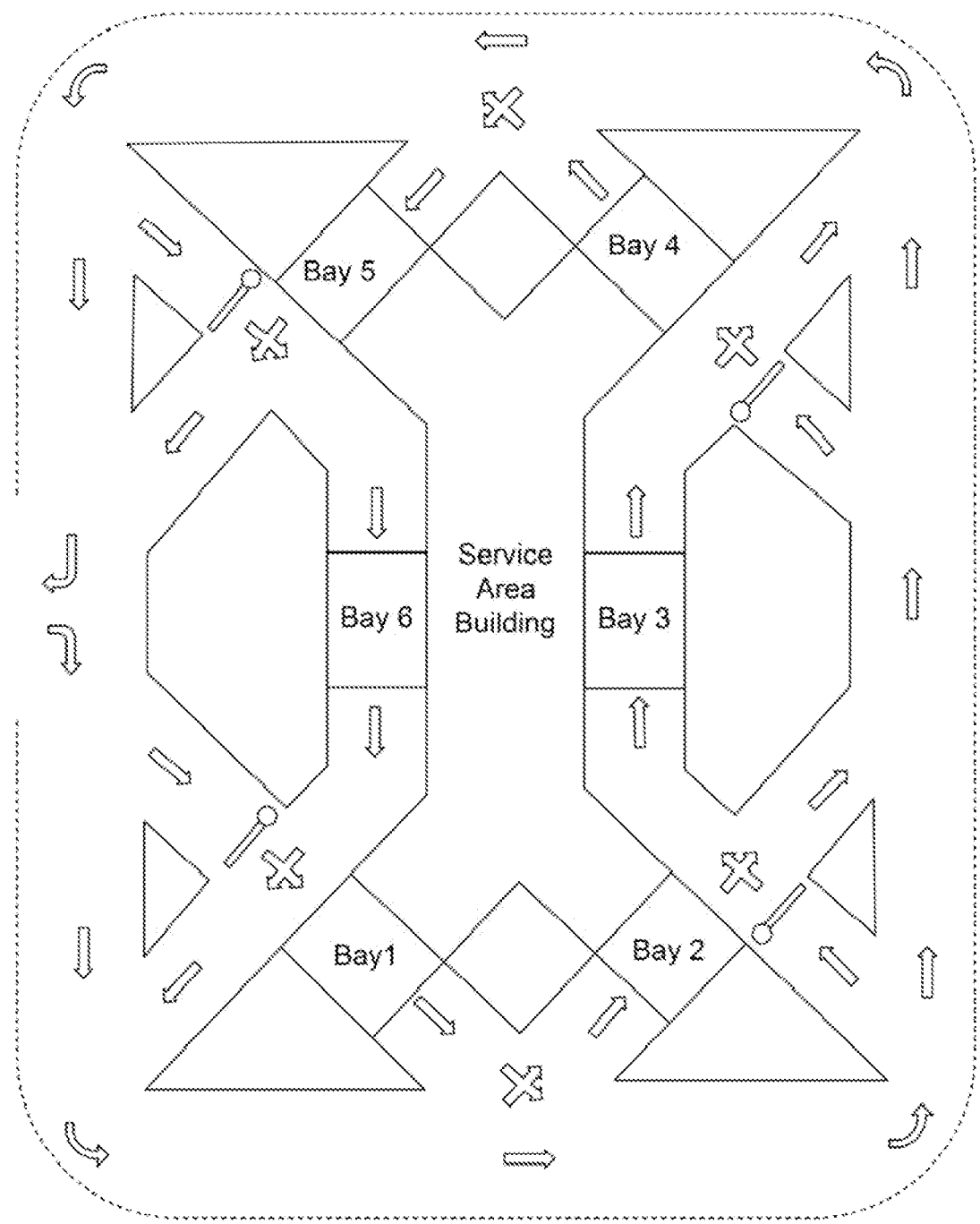
FIG. 21 is a schematic illustration of another alternate embodiment of a DTM building of the present disclosure having six consult bays.

In FIG. 20, a rectangular service area building has six consult bays attached thereto. In FIG. 21, an "X" shaped service area building has six consult bays attached thereto It is foreseen however that additional bays can be located along additional sides of the service area building depending on the length of the sides and clearance for traffic flow. In the embodiments of FIGS. 20 and 21, the path of cars entering and exiting the bays do intersect. As such, traffic gates are provided to regulate the flow of traffic though the intersections. Alternatively, bay doors can be synced to regulate the flow of traffic.

In general, one or more consult bays could be provided on each side of a multi-sided service area structure; e.g., a triangular service area could have three consult bays, while a pentagon building could have five consult bays. Each bay could have its own exam room and restroom, or could share an exam room and restroom with one or more consult bays. Parking spaces can be suitably located adjacent to or near by the building.

The building structure preferably is efficient and cost effective, using standard dimensions that other drive in/drive out facilities employ in their construction. For example, drive-through aisles shall have a minimum ten (10' 0") foot interior radius at curves and a minimum twelve (12' 0") foot width; drive-up windows and remote tellers shall provide at least sixty (60' 0") feet of stacking space for each facility, as measured from the service window or unit to the entry point into the drive-up lane; each drive-through entrance/exit shall be at least fifty (50' 0") feet from an intersection of public rights-of-way, measured at the closest intersecting curbs, and at least twenty-five (25' 0") feet from the curb-cut on an adjacent property; each entrance to an aisle and the direction of traffic flow shall be clearly designated by signs and pavement markings; and each drive-through aisle shall be separated from the circulation routes necessary for ingress or egress from the property, or access to a parking space. These dimensions may vary depending on the requirements of any applicable municipal codes.

While the embodiment(s) disclosed herein are illustrative of the structure, function and operation of the exemplary methods, systems, and building structures/architecture, it should be understood that various modifications may be made thereto with departing from the teachings herein. Further, the components of the methods, systems, and building structures/architecture disclosed herein can take any suitable form including any suitable applications, hardware, software, or other components capable of adequately performing their respective intended functions, as may be known in the art.

While the foregoing and following discussion presents the teachings in an exemplary fashion with respect to the disclosed methods, systems, and building structures/architecture for DTM, it will be apparent to those skilled in the art that the present disclosure may apply to other methods and systems for healthcare. Further, while the foregoing has described what are considered to be the best mode and/or other examples, it is understood that various modifications may be made therein and that the subject matter disclosed herein may be implemented in various forms and examples, and that the methods, systems, and building structures/architecture may be applied in numerous applications, only some of which have been described herein.

What is claimed is:

1. A building for drive through medicine for human healthcare, comprising:
    a single, rectangular building structure comprising four outer walls;
    a lobby inside the four outer walls of the single, rectangular building structure; and
    at least three drive-in consult bays each attached to a different one of the four outer walls of the single building structure, wherein at least one of the at least three drive-in consult bays is oriented perpendicular to at least one other of the at least three drive-in consult bays;
    a separate entry path leading to each of the at least three drive-in consult bays, wherein each separate entry path is configured not to cross paths with any other separate entry path;
    a separate exit path leading from each of the at least three drive-in consult bays, wherein each separate exit path is configured not to cross paths with any other separate exit path;
    wherein each separate entry path is configured not to cross paths with any separate exit path;
    wherein each of the at least three drive-in consult bays includes an entranceway to the lobby and is configured to enclose a single vehicle only;
    wherein each of the at least three drive-in consult bays is accessible by vehicle without interference from the other of the at least three drive-in consult bays; and
    wherein each separate entry and separate exit path of each of the at least three drive-in consult bays is situated along a different one of the at least four outer walls of the single, rectangular building structure.

2. The building of claim 1, further comprising a telemedicine device in each of the at least three drive-in consult bays for communicating directly with a patient.

3. The building of claim 1, wherein the lobby includes at least one exam room accessible from the at least three drive in consult bays.

4. The building of claim 1, wherein the lobby includes at least one restroom accessible from the at least three drive in consult bays.

5. The building of claim 1, wherein the lobby includes at least one work space having an opening to each of the at least three drive in consult bays.

6. The building of claim 1, further comprising a check-in station associated externally with each of the at least three drive in consult bays.

7. The building of claim 1, wherein the at least three drive-in consult bays comprises at least four drive-in consult bays.

8. A system for drive through medicine for human healthcare, comprising:
    a service road;
    at least three drive through lanes, wherein each drive through lane includes a separate entry path from the service road and a separate exit path to the service road;
    a private consult bay associated with each of the at least three drive through lanes, wherein the separate entry path from the service road for each of the at least three drive through lanes leads into and abuts with its associated private consult bay and the separate exit path to the service road of each of the at least three drive through lanes abuts with and leads away from its associated private consult bay; and
    a single, rectangular building structure having a single lobby being adjacent to each private consult bay, and having an opening to each private consult bay;
    wherein the service road surrounds the at least three drive through lanes, the private consult bay associated with each of the at least three drive through lanes, and the single lobby;
    wherein the single, rectangular building structure has four outer walls, and wherein each private consult bay is attached to a different outer wall of the building structure, and wherein at least one of the at least three drive though lanes is not parallel with at least one other of the at least three drive through lanes;
    wherein at least one of the private consult bays is oriented perpendicular to at least one other of the private consult bays;
    wherein each separate entry and separate exit path of each of the at least three drive-in through lanes is situated along a different one of the four outer walls of the single, rectangular building structure;
    wherein each private consult bay is configured to enclose therein a single vehicle only; and
    wherein each private consult bay is accessible by vehicle without interference from any of the other of the at least three drive through lanes.

9. The system of claim 8, further comprising a telemedicine device in each private consult bay or the lobby for communicating directly with a patient.

10. The system of claim 8, wherein the at least three drive through lanes comprises four drive through lanes.

11. The system of claim 8, further comprising a check-in station associated externally with each of the at least three drive through lanes.

12. The system of claim 8, wherein at least two of the at least three drive though lanes are not parallel with at least two others of the at least three drive through lanes.

13. The system of claim 8, further comprising at least one exam room and at least one restroom in the lobby.

14. A building for drive through medicine for human healthcare, comprising:
    a single, rectangular building structure, wherein the single, rectangular building structure comprises four outer walls surrounding a lobby;

a first drive-in consult bay attached to a first outer wall of the single, rectangular building structure and having an entrance to the lobby;

a first entry path leading to and abutting with the first drive-in consult bay;

a first exit path abutting with and leading from the first drive-in consult bay;

a second drive-in consult bay attached to a second outer wall of the single, rectangular building structure and having an entrance to the lobby;

a second entry path leading to and abutting with the second drive-in consult bay;

a second exit path abutting with and leading from the second drive-in consult bay;

a third drive-in consult bay attached to a third outer wall of the single, rectangular building structure and having an entrance to the lobby;

a third entry path leading to and abutting with the third drive-in consult bay;

a third exit path abutting with and leading from the third drive-in consult bay;

wherein the first entry path is configured not to cross paths with the second entry path and third entry path;

wherein the second entry path is configured not to cross paths with the first entry path and third entry path;

wherein the third entry path is configured not to cross paths with the first entry path and second entry path;

wherein the first exit path is configured not to cross paths with the second exit path and third exit path;

wherein the second exit path is configured not to cross paths with the first exit path and third exit path;

wherein the third exit path is configured not to cross paths with the first exit path and second exit path;

wherein the first drive-in consult bays is oriented perpendicular to at least one of the second drive-in consult bay and the third drive-in consult bay;

wherein the second drive-in consult bays is oriented perpendicular to at least one of the first drive-in consult bay and the third drive-in consult bay;

wherein the third drive-in consult bays is oriented perpendicular to at least one of the first drive-in consult bay and the second drive-in consult bay;

wherein the first entry path, the first drive-in consult bay and the first exit path are situated along a first one of the four outer walls of the single, rectangular building structure;

wherein the second entry path, the second drive-in consult bay and the second exit path are situated along a second one of the four outer walls of the single, rectangular building structure; and wherein the third entry path, the third drive-in consult bay and the third exit path are situated along a third one of the four outer walls of the single, rectangular building structure.

15. The building of claim 14, further comprising a fourth drive-in consult bay attached to a fourth outer wall of the single, rectangular building structure and having an entrance to the lobby, a fourth entry path leading to and abutting with the fourth drive-in consult bay, and a fourth exit path abutting with and leading from the fourth drive-in consult bay, wherein the fourth entry path is configured not to cross paths with the first entry path, second entry path and third entry path, and wherein the fourth exit path is configured not to cross paths with the first exit path, second exit path and third exit path; wherein the fourth drive-in consult bays is oriented perpendicular to at least two of the first drive-in consult bay, the second drive-in consult bay and the third consult bay; and wherein the fourth entry path, the fourth drive-in consult bay and the fourth exit path are situated along a fourth one of the four outer walls of the single, rectangular building structure.

* * * * *